A United States Patent [19]

Drent et al.

[11] Patent Number: 4,786,443
[45] Date of Patent: Nov. 22, 1988

[54] PROCESS FOR THE CARBONYLATION OF OLEFINICALLY UNSATURATED COMPOUNDS WITH A PALLADIUM CATALYST

[75] Inventors: Eit Drent; Simon A. J. van Langen; Leonardus Petrus, all of Amsterdam, Netherlands

[73] Assignee: Shell Oil Company, Houston, Tex.

[21] Appl. No.: 165,052

[22] Filed: Mar. 7, 1988

[30] Foreign Application Priority Data

Mar. 11, 1987 [GB] United Kingdom ................ 8705699

[51] Int. Cl.$^4$ ............................................. C07C 53/12
[52] U.S. Cl. .................... 260/549; 260/410.6; 260/546; 260/548; 562/406; 562/422
[58] Field of Search .................... 260/410.6, 546, 548; 562/406, 422

[56] References Cited

U.S. PATENT DOCUMENTS

| 2,607,787 | 8/1952 | Mason | 260/549 |
|---|---|---|---|
| 2,945,286 | 1/1950 | Brubaker | 260/63 |
| 3,689,460 | 9/1972 | Nozaki | 260/63 |
| 3,694,412 | 9/1972 | Nozaki | 260/63 |
| 3,887,595 | 6/1975 | Nozaki | 260/410.6 |
| 4,115,444 | 9/1974 | Rizkalla | 260/549 |
| 4,335,059 | 6/1982 | Rizkalla | 260/549 |
| 4,430,273 | 2/1984 | Erpenbach | 260/549 |
| 4,474,978 | 10/1984 | Drent et al. | 560/24 |
| 4,629,809 | 12/1986 | Vanderpool | 260/549 |
| 4,634,793 | 1/1987 | Drent | 560/243 |

FOREIGN PATENT DOCUMENTS

| 0106379 | 4/1984 | European Pat. Off. . |
|---|---|---|
| 0121965 | 10/1984 | European Pat. Off. . |
| 0181014 | 10/1984 | European Pat. Off. . |
| 0190473 | 8/1986 | European Pat. Off. . |
| 0213671 | 3/1987 | European Pat. Off. . |
| 2450965 | 4/1976 | Fed. Rep. of Germany . |
| 3144772 | 5/1983 | Fed. Rep. of Germany . |
| 2058074 | 4/1961 | United Kingdom . |
| 1081304 | 8/1967 | United Kingdom . |

OTHER PUBLICATIONS

Kirk Othmer Encyclopedia of Chemical Technology, Second Edition, vol. 12, p. 132, 1967.

Primary Examiner—Paul J. Killos

[57] ABSTRACT

Process for the carbonylation of olefins with CO in the presence of water, an alcohol and/or a carboxylic acid in the presence of a catalyst composition based on
(a) a Pd compound,
(b) a protonic acid, and
(c) a phosphine $PR^1R^2R^3$ in which $R^1$ is a heterocyclic ring having 5-6 atoms and containing $\geq 1$ hetero N atom and $R^2$ and $R^3$ are $R^1$ or an aryl group.

20 Claims, No Drawings

PROCESS FOR THE CARBONYLATION OF OLEFINICALLY UNSATURATED COMPOUNDS WITH A PALLADIUM CATALYST

FIELD OF THE INVENTION

The invention relates to a process for the carbonylation of an olefinically unsaturated compound with carbon monoxide in the presence of water, an alcohol and/or a carboxylic acid.

BACKGROUND OF THE INVENTION

European Patent Specification No. 0,106,379 discloses a process in which an olefinically unsaturated compound is carbonylated with carbon monoxide in the presence of water, and alcohol and/or a carboxylic acid, a palladium catalyst, at least 5 mol or a phosphine $PR^1R^2R^3$ in which $R^1$, $R^2$ and $R^3$ each represent an optionally, substituted aryl group, per gram-atom of palladium, and, as promoter, an acid with a pKa<2 (at 18° C. in aqueous solution), except hydrohalogenic and carboxylic acids.

Research carried out by the Applicant into these processes has shown that the activity of the catalyst composition can be considerably enhanced while retaining a very high selectivity to carbonylated products, when an organic phosphine belonging to a special group is used. The selectivity to a certain compound, expressed in a percentage, is defined herein as 100×a:b in which "a" is the amount of starting olefinically unsaturated compound that has been converted into that certain compound and "b" is the total amount of starting olefinically unsaturated compound that has been converted.

SUMMARY OF THE INVENTION

The present invention provides a process for the carbonylation of an olefinically unsaturated compound which comprises reacting an olefinically unsaturated compound with carbon monoxide and a reactant selected from the group consisting of water, an alcohol, a carboxylic acid and mixtures thereof, in the presence of a catalyst composition comprising:
(a) a palladium compound,
(b) a protonic acid, and
(c) an organic phosphine of the general formula I

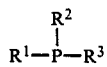

wherein $R^1$ represents a heterocyclic ring having 5 or 6 atoms in the ring which contains at least one hetero nitrogen atom in the ring and which may or may not be substituted and/or which may be part of a larger, condensed ring structure which may or may not be substituted and in which each of $R^2$ and $R^3$ has the same meaning as $R^1$ or represents an aryl group.

DESCRIPTION OF THE PREFERRED EMBODIMENTS

The special group of organic phosphines mentioned hereinbefore is that of the general formula I. The heterocyclic rings mentioned hereinbefore are preferably pyridyl, pyrazinyl, quinolyl, isoquinolyl, pyrimidinyl, pyridazinyl, indolizinyl, cinnolinyl, acridinyl, phenazinyl, phenanthridinyl, phenanthrolinyl, phthalazinyl, naphthyridinyl, quinoxalinyl or quinazolinyl groups.

Among these groups, pyridyl, pyrazinyl and pyridazinyl groups are preferred.

As used herein, the terms "heterocyclic rings" and "aryl groups" are used to refer to heterocyclic rings and aryl groups which can be unsubstituted or substituted with any substituents which do not interfere with the reaction. The heterocyclic rings and aryl groups can be substituted with one or more polar substituents or with one or more apolar substituents.

Examples of polar substituents which may be present are alkoxy groups, in particular those having not more than five carbon atoms and preferably methoxy and ethoxy groups; dimethylamino and diethylamino groups, in particular dimethylamino groups; chloro and fluoro atoms and trifluoromethyl, trichloromethyl and monochloromethyl groups. Examples of apolar substituents which may be present are alkyl groups having not more than five carbon atoms and preferably methyl and ethyl groups; other examples are n-propyl, 2-propyl and tert-butyl groups.

The substituted or unsubstituted aryl groups represented by $R^2$ and $R^3$ in the general formula I suitably contain not more than 18 carbon atoms in the ring system and are preferably phenyl groups, but can be anthryl or naphthyl groups.

Phosphines of the general formula I in which $R^1$ represents a pyridyl group, $R^2$ a pyridyl or phenyl group and $R^3$ a phenyl group are preferred.

According to a preferred embodiment of the present invention which not only allows very high selectivities to carbonylated products but also very high yields thereof, (2-pyridyl)diphenylphosphine is applied.

Other examples of suitable phosphines are:

di(p-methoxyphenyl)-2-pyridylphosphine
di(p-tolyl)-2-pyridylphosphine
di(o-methoxyphenyl)-2-pyridylphosphine
di(o-chlorophenyl)-2-pyridylphosphine
di(methoxyphenyl)-2-pyridylphosphine
di(m-chlorophenyl)-2-pyridylphosphine
di(p-methoxyphenyl)-3-pyridylphosphine
di(p-tolyl)-3-pyridylphosphine
di(o-methoxyphenyl)-3-pyridylphosphine
di(o-chlorophenyl)-3-pyridylphosphine
di(m-methoxyphenyl)-3-pyridylphosphine
di(m-chlorophenyl)-3-pyridylphosphine
di(p-methoxyphenyl)-4-pyridylphosphine
di(p-toly)-4-pyridylphosphine
di(o-methoxyphenyl)-4-pyridylphosphine
di(o-chlorophenyl)-4-pyridylphosphine
di(m-methoxyphenyl)-4-pyridylphosphine
di(m-chlorophenyl)-4-pyridylphosphine
diphenyl(3-methoxy-2-pyridyl)phosphine
diphenyl(4-methoxy-2-pyridyl)phosphine
diphenyl(4-chloro-2-pyridyl)phosphine
diphenyl(2-methoxy-3-pyridyl)phosphine
diphenyl(4-methoxy-3-pyridyl)phosphine
diphenyl(4-chloro-3-pyridyl)phosphine
diphenyl(3-methoxy-4-pyridyl)phosphine
diphenyl(3-chloro-4-pyridyl)phosphine
diphenyl(5-chloro-4-pyridyl)phosphine
diphenyl(5-methoxy-4-pyridyl)phosphine
di(p-toly)(3-methoxy-4-pyridyl)phosphine
di(p-toly)(3-chloro-4-pyridyl)phosphine
di(m-methoxyphenyl)(3-chloro-4-pyridyl)phosphine
di(m-methoxyphenyl)(3-methoxy-4-pyridyl)phosphine
di(m-chlorophenyl)(3-methoxy-4-pyridyl)phosphine di(p-toly)(3-methoxy-2-pyridyl)phosphine
di(p-tolyl)(3-chloro-2-pyridyl)phosphine
di(m-methoxyphenyl)(3-chloro-2-pyridyl)-phosphine
di(m-methoxyphenyl)(3-methoxy-2-pyridyl)phosphine
di(m-tert.butoxyphenyl)(3-chloro-2-pyridyl)phosphine
di(m-tert.butoxyphenyl)(3-methoxy-2-pyridyl)phosphine
di(m-tert.butoxyphenyl)(3-chloro-4-pyridyl)phosphine
di(m-tert.butoxyphenyl)(3-methoxy-4-pyridyl)phosphine
di(m-tert.butoxyphenyl)(2-methoxy-3-pyridyl)phosphine
di(m-tert.-butoxyphenyl)(2-chloro-3-pyridyl)phosphine
di(m-chlorophenyl)(2-methoxy-3-pyridyl)phosphine
di(m-chlorophenyl)(2-chloro-3-pyridyl)phosphine
di(o-chlorophenyl)(2-methoxy-3-pyridyl)phosphine
di(p-methoxyphenyl)-2-pyrimidinylphosphine
di(p-tolyl)-2-pyrimidinylphosphine
di(o-methoxyphenyl)-2-pyrimidinylphosphine
di(o-chlorophenyl)-2-pyrimidinylphosphine
di(m-methoxyphenyl)-2-pyrimidinylphosphine
di(p-methoxyphenyl)-2-pyridazinylphosphine
di(p-toly)-2-pyridazinylphosphine
di(o-methoxyphenyl)-2-pyridazinylphosphine
di(o-chlorophenyl)-2-pyridazinylphosphine
di(m-methoxyphenyl)-2-pyridazinylphosphine
di(p-methoxyphenyl)(3-methoxy-2-pyrimidinyl)phosphine
di(p-tolyl)(3-methoxy-2-pyridinyl)phosphine
di(o-chlorophenyl)(3-chloro-2-pyrimidinyl)phosphine
di(m-methoxyphenyl)(3-chloro-2-pyrimidinyl)phosphine
di(p-tolyl)(4-methoxy-3-pyridazinyl)phosphine
di(p-methoxyphenyl)(4-methoxy-3-pyridazinyl)phosphine
di(o-chlorophenyl)(4-methoxy-3-pyridazinyl)phosphine
phenyl-di(3-methoxy-2-pyridyl)phosphine
phenyl-di(4-methoxy-2-pyridyl)phosphine
phenyl-di(4-chloro-2-pyridyl)phosphine
phenyl-di(2-methoxy-3-pyridyl)phosphine
phenyl-di(4-methoxy-3-pyridyl)phosphine
phenyl-di(4-chloro-3-pyridyl)phosphine
phenyl-di(3-methoxy-4-pyridyl)phosphine
phenyl-di(3-chloro-4-pyridyl)phosphine
phenyl-di(5-chloro-4-pyridyl)phosphine
phenyl-di(5-methoxy-4-pyridyl)phosphine
phenyl-di(3-methoxy-2-pyrimidinyl)phosphine
phenyl-di(3-chloro-2-pyrimidinyl)phosphine
phenyl-di(4-methoxy-2-pyrimidinyl)phosphine
phenyl-di(4-methoxy-3-pyridazinyl)phosphine and
phenyl-di(4)chloro-3-pyridazinyl)phosphine As protonic acids, a large variety of acids or mixture of acids may be applied. Examples of such acids are orthophosphoric acid, pyrophosphoric acid, sulfuric acid, hydrohalogenic acids, benzene phosphonic acid, benzenesulfonic acid, p-toluenesulfonic acid, naphthalenesulfonic acid, toluenephosphonic acid, chlorosulfonic acid, fluorosulfonic acid, monochloroacetic acid, dichloroacetic acid, trichloroacetic acid, trifluoroacetic acid, oxalic acid, terephthalic acid, perchloric acid, 2-hydroxypropane-2-sulfonic acid trifluoromethanesulfonic acid and mixtures thereof. Among these acids p-toluenesulfonic acid and benzenephosphonic acid are preferred.

Where a non-carboxylic acid having a pKa greater than 2, measured at 18° C. in aqueous solution, and/or a sterically hindered carboxylic acid having a pKa below 4.5, also measured at 18° C. in aqueous solution, is applied, preferably at least 1 mol of such acids is used per mol of organic phosphine of the general formula I. Examples of preferred non-carboxylic acids having a pKa greater than 2 are benzenephosphonic sacid and orthophosphoric acid. Arsenic acid is another example of such acids. The carboxylic acid being sterically hindered means that atoms or groups of atoms are present which interfere with one another, thus counteracting esterification of the acid. Examples of such acids are 2,6-dimethylbenzonic acid and 2,6-diethylbenzoic acid. It is preferred to apply sterically hindered carboxylic acids having a pKa below 2. Among the sterically hindered carboxylic acids, preference is given to the sterically hindered benzoic acids such as, for example 2,6-dichlorobenzoic acid, 2,6-difluorobenzoic acid, 2,4,6-trifluorobenzoic acid, 2,4,6-trichlorobenzoic acid, 2,6-dibromobenzoic acid, 2,4,6-tribromobenzoic acid, 2,6-diiodobenzoic acid and 2,4,6-triiodobenzoic acid.

Hydrohalogenic acids may in principle, be used but they have the known disadvantage that they may cause a corrosive effect.

Both homogeneous and heterogeneous palladium compounds may be used in the process according to the present invention. Homogeneous compounds are preferred. Suitable homogeneous compounds are palladium salts of nitric acid, sulfuric acid and alkanoic acids having not more than 12 carbon atoms per molecule.

Salts of hydrohalogenic acids may, in principle, be used as well, but they have the drawback that the halogen ion may have a corrosive effect.

A palladium compound used by preference is palladium acetate. Moreover, palladium complexes may be used, for instance palladium acetylacetonate, tetrakistriphenylphosphinepalladium, bis(tri-o-tolyphosphine)palladium acetate, bis(triphenylphosphine)palladium sulfate, bis(diphenyl-2-pyridylphosphine)palladium acetate, tetrakisdiphenyl-2-pyridylphosphine palladium, bis(di-o-tolylpyridyl)phosphinepalladium acetate and bis(diphenylpyridyl)phosphine palladium sulfate. Palladium on charcoal and palladium bonded to an ion exchanger—for instance an ion exchanger comprising sulfonic acid groups—are examples of suitable heterogeneous catalysts.

The quantity of catalyst composition used in the present process may vary within wide ranges. Preferably, per mol of olefinically unsaturated compound to be carbonylated, such as quantity of catalyst is used as to contain in the range of from $10^{-7}$ to $10^{-1}$ and in particular from $10^{-6}$ to $10^{-3}$ gram-atom of palladium.

The organic phosphine may be used in an amount per gram-atom palladium which is not critical and may vary within wide ranges. Preferably, this amount is in the range of from 2 to 500 mol per gram-atom palladium. In general, amounts of more than 1000 mol organic phosphine per gram-atom of palladium are not necessary.

The protonic acid may be used in an amount per equivalent of organic phosphine which is not critical and may vary within wide ranges. Preferably, this amount is in the range of from 0.1 to 50 equivalents per equivalent of organic phosphine.

It has, furthermore, been found that the reaction rate in the process according to the present invention can be maintained very high by the application of a catalyst stabilizer in catalytic amounts. Examples of such stabilizers are mentioned in Netherlands Patent Application No. 8603302, filed Dec. 24, 1986. N-methylpyrrolidone is an attractive example of such a catalyst stabilizer.

It is not necessary to carry out the process according to the present invention in the presence of a separate solvent since a large excess of one of the reactants, usually the alcohol, forms a suitable liquid phase. If required, however, a separate solvent may be used. Any inert solvent may be used for this purpose. Examples of suitable solvents are dimethyl sulfoxide, diisopropyl sulfone, tetrahydrothiophene 1,1-dioxide (also referred to a "sulfolane"), 2-methylsulfolane, 3-methylsulfolane, 2-methyl-4-butylsulfolane; aromatic hydrocarbons such as benzene, toluene and the three xylenes; esters such as methyl acetate and gamma-butyrolactone; ketones such as acetone and methyl isobutyl ketone; ethers such as anisole, 2,5,8-trioxanonane (also referred to as "diglyme"), diphenyl ether and diisopropyl ether.

The carbonylation according to the invention is preferably carried out at a temperature in the range of from 20° to 200° C., in particular from 50° to 150° C. The overall pressure preferably lies between 1 and 100, in particular 5 and 75 bar.

The molar ratio of the olefinically unsaturated compound to water, alcohol or carboxylic acid is not critical. The molar ratio between hydroxy groups and olefinic double bonds may lie for instance between 0.01:1 and 100:1, and will usually be between 0.1:1 and 10:1. When using a mono-olefin and either water, a monohydric alcohol or a monobasic acid, preference is usually given to the use of an excess of the hydroxy compound mentioned. However, when using a polyhydric alcohol or a polybasic acid to prepare a polyester or a polyanhydride, it will generally be necessary to use an excess of olefinic compound.

"Olefinically unsaturated compound" as used herein, refers to an unsubstituted or a substituted alkene or cycloalkene preferably having 2–30, and in particular 2–20, carbon atoms per molecule and preferably 1–3 carbon-carbon double bonds per molecule. The alkene or cycloalkene may be substituted, for instance, with one or more halogen atoms or cyano, ester, alkoxy, hydroxy, carboxy or aryl groups. If the substituents are not inert under the reaction conditions, the carbonylation reaction may be accompanied with other reactions. For instance, the carbonylation of allyl alcohol is accompanied with esterification of the hydroxy group. Examples of suitable olefinic compounds are ethene, propene, 1-butene, 2-butene, isobutene, the isomeric pentenes, hexenes, octenes and dodecenes, 1,5-cyclooctadiene, cyclododecene, 1,5,9-cyclododecatriene, allyl alcohol, methyl acrylate, ethyl acrylate, methyl methacrylate, acrylonitrile, acrylamide, N,N-dimethylacrylamide, vinyl chloride, allyl chloride, acrolein, oleic acid, methyl allyl ether and styrene. Very good results have been obtained with ethylene.

The alcohols or carboxylic acids used in the process according to the invention may be aliphatic, cycloaliphatic or aromatic and may be substituted with one or more substituents, such as mentioned hereinbefore in connection with the olefinically unsaturated compounds to be used as starting material. The alcohol may therefore also be a phenol. The alcohols or carboxylic acids preferably contain not more than 20 carbon atoms per molecule. Examples of suitable alcohols are methanol, ethanol, propanol, isobutanol, tert.butanol, stearyl alcohol, benzyl alcohol, cyclohexanol, allyl alcohol, a chlorocapryl alcohol, ethylene glycol, 1,2-propanediol, 1,4-butanediol, glycerol, polyethylene glycol, 1,6-hexanediol, phenol and cresol. Examples of suitable carboxylic acids are formic acid, acetic acid, propionic acid, butyric acid, caproic acid, trimethylacetic acid, benzoic acid, caprylic acid, succinic acid, adipic acid and hydroxycaproic acid. Special preference is given to alkanols and carboxylic acids having 1–10 carbon atoms per molecule. If the alcohol or the carboxylic acid has more than one hydroxy group or carboxy group, different products may be formed, depending on the molar ratios existing between the reagents. For instance, depending on the quantity of olefinically unsaturated compound used, either a mono-ester or a diester may be produced from glycerol. Another example of a polyvalent alcohol is a sugar.

The products formed in the process according to the invention may be further reacted if desired. For instance, the carbonylation of an olefion, when conducted in the presence of water, yields a carboxylic acid which, by reaction with a further quantity of olefin, may form a carboxylic anhydride. When the carbonylation is carried out in the presence of an alcohol, it yields an ester which, when water is present as well, may hydrolyze to form an acid and an alcohol, each of which may again react with an olefin. When the carbonylation is carried out in the presence of a carboxylic acid, it yields a carboxylic anhydride which, when water is present as well, may hydrolyze to form one or more carboxylic acids which in their turn may react with a further quantity of olefin.

Reaction of an alkanecarboxylic acid having n+1 carbon atoms with an olefin having n carbon atoms yields the symmetrical anhydride of the alkanecarboxylic acid having n+1 carbon atoms. This anhydride may optionally be hydrolyzed, half of the carboxylic acid formed may be collected as a product and the other half recycled to the carbonylation reactor. The process thus leads to the conversion of an olefin having n carbon atoms into a carboxylic acid having n+1 carbon atoms.

In the process according to the invention, the carbon monoxide may be used pure or diluted with an inert gas, such as nitrogen, noble gases or carbon dioxide. Generally the presence of more than 10% v of hydrogen is undesirable, since under the reaction conditions it may cause hydrogenation of the olefinic compound. Generally preference is given to the use of carbon monoxide or a carbon monoxide-containing gas which contains less than 5% v of hydrogen. Suitably, a molar ratio carbon monoxide to olefinically unsaturated compound in the range of from 0.1:1 to 10:1 is used.

During the process according to the present invention one or more of the three components of the catalyst composition may be supplied, continuously or intermittently, to compensate for possible losses thereof, if any such losses might occur.

The following Examples further illustrate the invention and are not intended to be construed as limiting the scope of the invention.

EXAMPLE 1

Propionic anhydride was prepared as follows. A magnetically stirred Hastelloy C autoclave ("Hastelloy" is a trade mark) of 250 ml capacity was charged with a catalyst solution comprising 50 ml of propionic anhydride, 10 ml of propionic acid, 0.1 mmol of palladium acetate, 3 mmol of p-toluenesulfonic acid, and 5 mmol of (2-pyridyl)diphenylphosphine.

After any air present in the autoclave had been removed by evacuation, ethene was introduced with pressure until a pressure of 20 bar was reached, followed by carbon monoxide until a pressure of 50 bar was reached.

Subsequently, the contents of the autoclaves were heated to 105° C. After 1 h the carbonylation was terminated by cooling to room temperature and then releasing the pressure. Analysis of the contents of the autoclave by means of gas-liquid chromatography showed that propionic anhydride had been formed with a rate of 1340 mol per mol palladium per hour and that the conversion of propionic acid was 76%.

Comparative Experiment A

Example 1 was repeated with the differences that triphenylphosphine (5 mmol) instead of (2-pyridyl)diphenylphosphine (5 mmol) and a temperature of 130° C. instead of 105° C. were used. Propionic anhydride had been formed with a rate of 380 mol per mol palladium per hour and the conversion of propionic acid was 24%.

Comparison of Example 1 carried out at 105° C. and using a catalyst composition which contained a phosphorus/nitrogen compound as the component (c) with Comparative Experiment A carried out at 130° C. and using a catalyst composition which contained a triarylphosphine as the component (c) shows that when the process according to the present invention is carried out a higher reaction rate can be achieved at lower temperatures.

EXAMPLE 2

Example 1 was repeated with the difference that N-methylpyrrolidone (58 mmol) was also present. Propionic anhydride has been formed with a rate of 1375 per mol palladium per hour and the conversion of propionic acid was 88%.

Comparison of Example 1 carried out in the absence of a stabilizer with Example 2 carried out in the presence of N-methylpyrrolidone as a stabilizer shows that the presence of a stabilizer allows a higher reaction rate.

EXAMPLE 3

Phenyl propionate was prepared in substantially the same way as propionic anhydride in Example 1, the differences being:
(a) the catalyst solution contained
    40 ml of dimethyl carbonate,
    10 g of phenol,
    0.1 mmol of palladium acetate,
    2 mmol of p-toluenesulfonic acid,
3 mmol of (2-pyridyl)diphenylphosphine, and
(b) the reaction temperature was 120° C.

The reaction rate was 150 g phenyl propionate per g palladium per hour and the selectivity to phenyl propionate was 95%.

Comparative Experiment B

Example 3 was repeated with the difference that triphenylphosphine (3 mmol) instead of (2-pyridyl)diphenylphosphine (3 mmol) was used. The reaction rate was 75 g phenyl propionate per g palladium per hour.

Comparison of Example 3 carried out using a catalyst composition which contained a phosphorus/nitrogen compound as the component (c) with Comparative Experiment B using a catalyst composition which contained a triarylphosphine as the component (c) shows that when the process according to the present invention is carried out a higher reaction rate can be achieved.

EXAMPLE 4

Propionic acid was prepared in substantially the same way as propionic anhydride in Example 1, the difference being:
(a) the catalyst solution contained
    40 ml of diglyme
    10 ml of water,
    0.1 mmol of palladium acette,
    2 mmol of p-toluenesulfonic acid, and
    3 mmol of (2-pyridyl)diphenylphosphine, and
(b) the reaction temperature was 100° C. instead of 105° C.

Propionic acid had been formed with a rate of 1400 g per g palladium per h and the selectivity to this acid was more than 95%.

EXAMPLE 5

Propionic anhydride was prepared in substantially the same way as in Example 1, the differences being:
(a) the catalyst solution contained
    50 ml of anisole,
    10 ml of propionic acid,
    0.1 mmol of palladium acetate,
    2 mmol off p-toluenesulfonic acid, and
3 mmol of (2-pyridyl)diphenylphosphine, and
(b) the reaction temperature was 90° C., the partial pressures of ethylene and carbon monoxide were 30 bar each and the reaction time was 3 hours.

Propionic anhydride had been formed with a rate of 1500 g per g palladium per hour and with a selectivity of more than 95%.

EXAMPLE 6

Propionic anhydride was prepared in substantially the same way as in Example 1, the differences being:
(a) the catalyst solution contained
    50 ml of propionic anhydride,
    10 ml of propionic acid,
    0.05 mmol of palladium acetate,
    1.5 mmol of p-toluenesulfonic acid, and
    2.5 mmol of di(2-pyridyl)phenylphosphine, and
(b) the reaction temperature was 120° C. instead of 105° C.

Propionic anhydride had been formed with a rate of 890 mol per gram-atom palladium per hour and the conversion of propionic acid was 37%.

EXAMPLE 7

Ethylene was carbonylated in substantially the same way as in Example 1, the differences being:
(a) the catalyst solution contained
    40 ml of anisole,
    20 ml of acetic acid,
    0.1 mmol of palladium acetate,
    2 mmol of P-toluenesulfonic acid, and
    3 mmol of (2-pyridyl)diphenylphosphine, and
(b) the reaction temperature was 90° C. instead of 105° C. and the reaction time was 5 hours instead of 1 hour.

Carbonylation products had been formed with a rate of 500 mol per gram-atom palladium per hour and these products consisted of 80 mmol of acetic propionic anhydride, 120 mmol of acetic anhydride, 110 mmol of propionic acid and about 10 mmol of propionic anhydride.

EXAMPLE 8

Ethylene was carbonylated in substantially the same way as in Example 7, the differences being that 30 ml of methanol and 10 ml of propionic acid were present instead of 20 ml of acetic acid and that the reaction temperature was 95° C. instead of 90° C.

Methyl propionate had been formed with a rate of 1000 mol per gram-atom palladium per hour.

We claim:

1. A process for the carbonylation of an olefinically unsaturated compound which comprises reacting said olefinically unsaturated compound with carbon monoxide and a reactant selected from the group consisting of water, an alcohol, a carboxylic acid and mixtures thereof in the presence of a catalyst composition comprising:
   (a) a palladium compound,
   (b) a protonic acid, and
   (c) an organic phosphine of the general formula I

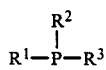

wherein $R^1$ represents a heterocyclic ring having 5 or 6 carbon atoms in the ring which contains at least one hetero nitrogen atom in the ring and wherein each of $R^2$ and $R^3$ has the same meaning as $R^1$ or represents an aryl group.

2. The process of claim 1 wherein said heterocyclic ring is part of a larger, condensed ring structure.

3. The process of claim 1 wherein said heterocyclic ring is selected from the group consisting of quinolyl, isoquinolyl, pyrimidinyl, indolizinyl, cinnolinyl, acridinyl, phenazinyl, phenanthridinyl, phenanthrolinyl, phthalazinyl, naphthyridinyl, quinoxalinyl, quinazolinyl groups and mixtures thereof.

4. The process of claim 1 wherein said heterocyclic ring is selected from the group consisting of pyridyl, pyrazinyl and pyridazinyl groups.

5. The process of claim 1 wherein $R^2$ and $R^3$ each represent a phenyl group.

6. The process of claim 1 wherein said heterocyclic ring and said aryl groups are substituted with one or more polar substituents.

7. The process of claim 6 wherein said polar substituents are selected from the group consisting of alkoxy groups having not more than five carbon atoms, chloro atoms, fluoro atoms, trifluoromethyl, trichloromethyl, monochloromethyl, diethylamino groups and mixtures thereof.

8. The process of claim 6 wherein said substituents are selected from the group consisting of methoxy, ethoxy, methyl, ethyl and dimethylamino groups.

9. The process of claim 1 wherein said heterocyclic ring and said aryl groups are substituted with one or more apolar groups.

10. The process of claim 9 wherein said substituents are alkyl groups having not more than five carbon atoms.

11. The process of claim 1 wherein a phosphine of the general formula I is applied in which $R^1$ represents pyridyl, $R^2$ is selected from the group consisting of pyridyl and phenyl, and $R^3$ represents phenyl.

12. The process of claim 1 wherein said protonic acid is selected from the group consisting of p-toluenesulfonic acid and benzenephosphonic acid.

13. The process of claim 1 wherein said palladium compound is palladium acetate.

14. The process of claim 1 wherein said palladium compound is used in an amount ranging from about $10^{-7}$ to about $10^{-1}$ gram-atom palladium per mol olefinically unsaturated compound.

15. The process of claim 1 wherein said organic phosphine is used in an amount ranging from about 2 to about 500 mol per gram-atom palladium.

16. The process of claim 1 wherein said protonic acid is used in an amount ranging from about 0.1 to about 50 equivalents per equivalent of organic phosphine.

17. The process of claim 1 wherein said process is carried out in the presence of a catalyst stabilizer.

18. The process of claim 1 wherein an amount of water, alcohol and/or carboxylic acid in the range of from about 0.01 to about 100 mol per mol of olefinically unsaturated compound is used.

19. The process of claim 1 wherein said process is carried out at a pressure in the range of from about 1 to about 100 bar and a temperature in the range of from 20° C. to 200° C.

20. The process of claim 1 wherein said olefinically unsaturated compound is selected from the group consisting of an alkene having in the range of from 2 to about 30 carbon atoms per molecule and a cycloalkene having in the range of from 2 to about 30 carbon atoms per molecule.

* * * * *